United States Patent
Smith et al.

(10) Patent No.: US 10,945,877 B2
(45) Date of Patent: Mar. 16, 2021

(54) THERMOREGULATING GELPACK

(71) Applicant: 6343326 Manitoba Ltd., Winnipeg (CA)

(72) Inventors: Jeff Smith, Winnipeg (CA); Rodney Tittle, Winfield, AL (US); Brett Wilson, Winnipeg Beach (CA)

(73) Assignee: 6343326 Manitoba Ltd., Winnipeg (CA)

( * ) Notice: Subject to any disclaimer, the term of this patent is extended or adjusted under 35 U.S.C. 154(b) by 430 days.

(21) Appl. No.: 15/729,174

(22) Filed: Oct. 10, 2017

(65) Prior Publication Data

US 2018/0098879 A1   Apr. 12, 2018

Related U.S. Application Data (60) Provisional application No. 62/406,131, filed on Oct. 10, 2016.

(51) Int. Cl.
| | | |
|---|---|---|
| *A61F 7/02* | (2006.01) | |
| *A61F 7/10* | (2006.01) | |
| *A61F 7/00* | (2006.01) | |
| *F25D 3/00* | (2006.01) | |
| *A41D 13/005* | (2006.01) | |

(52) U.S. Cl.
CPC .................. *A61F 7/02* (2013.01); *A61F 7/10* (2013.01); *F25D 3/00* (2013.01); *A41D 13/0058* (2013.01); *A61F 2007/0018* (2013.01); *A61F 2007/0098* (2013.01); *A61F 2007/022* (2013.01); *A61F 2007/0219* (2013.01); *A61F 2007/0225* (2013.01); *A61F 2007/0233* (2013.01); *A61F 2007/0234* (2013.01); *A61F 2007/0238* (2013.01); *A61F 2007/0246* (2013.01); *A61F 2007/0247* (2013.01); *A61F 2007/0249* (2013.01); *A61F 2007/0255* (2013.01); *A61F 2007/108* (2013.01)

(58) Field of Classification Search
CPC combination set(s) only.
See application file for complete search history.

(56) References Cited

U.S. PATENT DOCUMENTS

| | | |
|---|---|---|
| 3,545,230 A | 12/1970 | Morse |
| 3,736,769 A | 6/1973 | Petersen |
| 5,146,625 A | 9/1992 | Steele et al. |
| 5,227,230 A | 7/1993 | McGlade |
| 5,305,471 A | 4/1994 | Steele et al. |
| 5,484,448 A | 1/1996 | Steele et al. |
| 6,185,742 B1 | 2/2001 | Doherty |

(Continued)

FOREIGN PATENT DOCUMENTS

CN   203182051 U   9/2013

*Primary Examiner* — Joseph A Stoklosa
*Assistant Examiner* — Adam J Avigan
(74) *Attorney, Agent, or Firm* — Coats + Bennett, PLLC (57) ABSTRACT

A gel-pack has a plurality of self-contained components organized as layers in an interior chamber of the gel-pack. Each layer may be inserted into, and removed from, the interior chamber individually. The components include a solid-state gel layer that stores thermal energy, a first radiant energy barrier that prevents the transfer of thermal energy radiating from an exterior of the gel-pack into the solid-state gel layer, and a second radiant energy barrier that reflects the thermal energy radiating from the user's body into the solid-state gel layer.

17 Claims, 5 Drawing Sheets

(56) References Cited

U.S. PATENT DOCUMENTS

| | | |
|---|---|---|
| 6,233,945 B1 | 5/2001 | Kohout |
| 6,319,599 B1 | 11/2001 | Buckley |
| 7,739,748 B2 | 6/2010 | Nilforushan et al. |
| 8,220,074 B2 | 7/2012 | Sutker |
| 8,671,464 B2 | 3/2014 | Silverberg |
| 2006/0253954 A1 | 11/2006 | Music |
| 2011/0041229 A1 | 2/2011 | Niemi et al. |
| 2011/0313497 A1 | 12/2011 | McFarlane |
| 2013/0000874 A1 | 1/2013 | Colburn et al. |
| 2015/0059390 A1* | 3/2015 | Hayes ............... A61F 7/02 62/259.3 |
| 2016/0255884 A1* | 9/2016 | Chaumont ......... A41D 13/0058 |

* cited by examiner

THERMOREGULATING GELPACK

RELATED APPLICATIONS

This application claims priority to U.S. Provisional Application Ser. No. 62/406,131 entitled "Removable, Rechargeable, Thermoregulating Radiant Gel-Pack." The '131 application was filed on Oct. 10, 2016 and is incorporated herein by reference in its entirety.

FIELD OF THE INVENTION

This present disclosure relates generally to thermo-regulating gel-packs, and more particularly, to thermoregulating gel-packs comprising multiple replaceable components.

BACKGROUND

There are many different environmental and bio-physiologic conditions that can cause elevated body temperatures. By way of example, temperatures associated with industries such as nuclear plants, foundries, underground mines, and chemical plants can reach uncomfortable, and at times intolerable, levels. Further, the mandated protective clothing for workers in these industries, as well as some of the pollutants found in materials used by these industries, can exacerbate the conditions that elevate body temperatures. For example, pollutants such as asbestos fibers and radiologic contamination may cause or aggravate an unsafe elevation in body temperature and loss of body fluids.

Whether caused by exogenous environmental or intrinsic biogenic factors, or by layers of protective clothing, abnormally high body temperatures often result in discomfort, dehydration, nausea, dizziness, fainting spells, and mental impairment, among other undesirable physical signs and symptoms. Indeed, with high body core temperatures comes an increased risk of significant mistakes in judgment, absenteeism, down time, serious physical illness, or in some cases, death.

SUMMARY

Aspects of the present disclosure provide a multi-layer, thermo-regulating gel-pack configured to help maintain a user's desired body core temperature. In one aspect, the multiple layers of materials are arranged in a particular order. Each layer is a stand-alone component of the gel-pack, and is removable and rechargeable. The particular arrangement of the gel-pack layers is selected to control interior and exterior radiant energy interference, and to allow variable thermoregulation intensity over an extended duration of time.

In one embodiment of the present disclosure, a multi-layer gel-pack for regulating a core body temperature of a user comprises a casing and a plurality of components disposed as layers within the casing. The casing has a first surface that faces towards a user and an opposing second surface that faces away from the user. The plurality of components comprises a thermal energy storage component configured to store thermal energy radiating from a user's body, a first radiant energy barrier disposed between the thermal energy storage component and the second surface of the casing, and a second radiant energy barrier disposed between the thermal energy storage component and the first radiant energy barrier. The first radiant energy barrier is configured to prevent the transfer of thermal energy radiating from an exterior of the casing into the thermal energy storage component, and the second radiant energy barrier is configured to reflect the thermal energy radiating from the user's body into the thermal energy storage component.

In another embodiment of the present disclosure, a multi-layer gel-pack for regulating a core body temperature of a user includes a casing comprising an interior chamber formed between first and second exterior surfaces. The first exterior surface faces towards the user and the second exterior surface faces away from the user. The multi-layer gel-pack also includes a plurality of layers disposed within the chamber. These include a high thermal capacity (HTC) layer and first and second metallized reflective layers. The HTC layer comprises one or more individual compartments with each compartment comprising a gel configured to store thermal energy radiated by the user's body. The first metallized reflective layer is disposed within the interior chamber between the HTC layer and the casing, and reflects ambient thermal energy away from the HTC layer. The second metallized reflective layer is disposed within the interior chamber between the HTC layer and the first metallized reflective layer, and is configured to focus the thermal energy radiated by the user's body into the one or more individual compartments of the HTC layer.

Additionally, one embodiment of the present disclosure provides a method of assembling a multi-layer gel-pack for regulating a core body temperature of a user. In this embodiment, the method comprises inserting a thermal energy storage component into an interior of a casing, inserting a first radiant energy barrier into the interior of the casing between the thermal energy storage component and the casing, and inserting a second radiant energy barrier into the interior of the casing between the thermal energy storage component and the first radiant energy barrier. The thermal energy storage component is configured to store thermal energy that radiates from the user, while the first radiant energy barrier prevents the transfer of ambient thermal energy into the thermal energy storage component. The second radiant energy barrier reflects the thermal energy radiating from the user's into the thermal energy storage component.

Of course, those skilled in the art will appreciate that the present invention is not limited to the above contexts or examples, and will recognize additional features and advantages upon reading the following detailed description and upon viewing the accompanying drawings.

DETAILED DESCRIPTION

Embodiments of the present disclosure provides a gel-pack that utilizes a specific combination and order of layered materials to allow for the control of interior and exterior radiant energy interference coupled with variable thermo-regulation intensity and duration. More specifically, the particular ordering of the layers, as well as the properties of the different materials that comprise the layers, provides a multi-layer, rechargeable gel-pack having a controlled thermal energy transfer rate and duration. Further, each of the layers is a self-contained, removable component, and thus, each is individually replaceable within the gel-pack. As shown in more detail below, the gel-pack of the present disclosure is highly efficient, comfortable, and applicable to a wide variety of purposes. One such purpose is in regulating the body core temperature of a user such that it is maintained within a healthy, safe range.

By way of example only, one or more gel-packs may be inserted into pockets or cavities formed in an article of clothing worn by a person or animal. So positioned, the gel-packs regulate the core body temperature of the person or animal. As seen in more detail later, such articles of clothing include, but are not limited to, vests, scarves, hats, and footwear, for example, but also include blankets, medical devices (e.g., sleeves, etc.), and the like.

The particular combination and ordering of the layered materials in the gel-pack of the present disclosure provide benefits that conventional devices are not able to provide. For example, some conventional devices reduce body core temperatures using methods that utilize convection (i.e., by moving air over a local area of skin), evaporation (e.g., such as spraying a local area of skin with a highly volatile liquid or the natural perspiration control mechanism of the body), or conduction (i.e., the application of a solid, liquid, or gaseous medium having a temperature lower than that of skin tissue). Other conventional devices utilize varying forms of rechargeable thermal cores.

However, conventional devices lose energy very rapidly, and thus, quickly lose their ability to keep a user cool. Further, recharging conventional devices often requires a lot of time and another device that provides a large temperature differential (e.g., a freezer). The particular combination and ordering of the layered materials in the gel-pack of the present disclosure, however, allow for the control of exterior radiant energy interference, coupled with variable thermo-regulation intensity and duration. Additionally, the properties of the materials comprising the various component layers, along with the specific order of those component layers, produce a rechargeable device with controlled thermal energy transfer rates and duration that is highly efficient, comfortable and applicable to a variety of purposes.

Figure 1A:
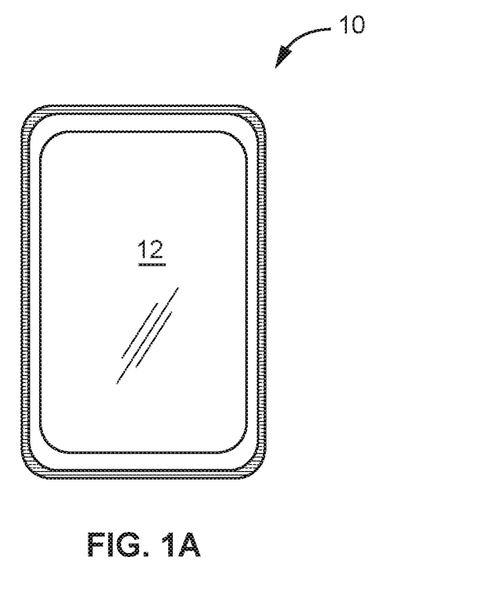
FIGS. 1A-1B are perspective front and back views, respectively, of a gel-pack device configured according to one embodiment of the present disclosure.
Figure 1B:
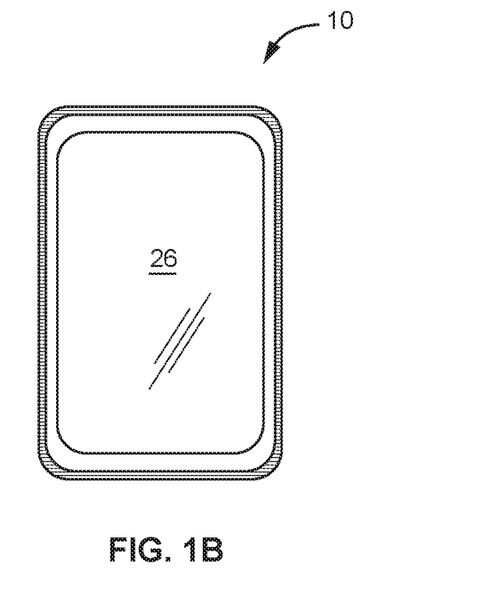

Turning now to the drawings, FIGS. 1A and 1B illustrate, respectively, the front and back surfaces of a multi-layer, rechargeable gel-pack 10 configured according to one embodiment of the present disclosure. Gel-pack 10 comprises a first shell layer 12 and a second shell layer 26 fixedly attached to each other at their peripheral edges. So attached, shell layers 12, 26 form an outer casing configured to contain a plurality of self-contained layers of material.

Figure 2:
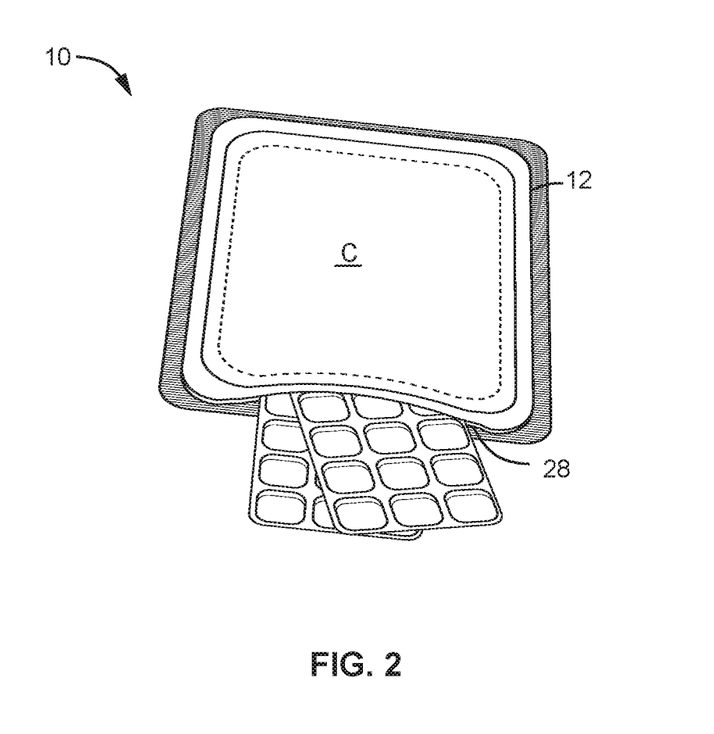
FIG. 2 is a perspective view of some stand-alone layers inserted into a gel-pack according to one embodiment of the present disclosure.

For example, as seen in FIG. 2, the first and second shell layers 12, 26 may be stitched or otherwise bonded together on three sides so as to form a pouch having an interior chamber C. The interior chamber C is sized and configured such that users are able to insert and remove each of a plurality of self-contained layers through an opening 28. Thus, each self-contained layer may be individually inserted into, and removed from, gel-pack 10 by a user. This facilitates the user's ability to replace and/or recharge one or more of the self-contained layers.

Those of ordinary skill in the art will appreciate that gel-pack 10 of the present disclosure need not be formed to include an opening 28. In other embodiments, for example, the first and second shell layers 12, 26 are attached to each other on all sides thereby forming a "closed" pouch that encases the multiple self-contained layers. In these embodiments, the layers forming the gel-pack 10 are inserted into the cavity or pouch in a specific arrangement during a manufacturing process prior to sealing any remaining peripheral sides. Thus, with these latter embodiments, a user may not be able to individually replace or recharge the individual layers; however, the user would still be able to swap one gel-pack 10 for another gel-pack 10, as will be seen in more detail later.

In still other embodiments, the first and second shells 12, 26 of gel-pack 10 may be attached together so as to form both a "closed" pouch that contains some of the self-contained layers, and an "open" pouch that allows a user to individually insert and remove other self-contained layers. In these embodiments, a user would be able to replace any self-contained layers disposed in the "open" part of the pouch via opening 28, as previously described, but would not be able to remove or replace any of the self-contained layers disposed in the "closed" portion of the pouch.

As seen in the figures, gel-pack 10 is illustrated as being rectangular or trapezoidal in shape. However, those of ordinary skill in the art will readily appreciate that gel-pack 10 is not limited only to these shapes. Rather, the particular shape and size of a gel-pack 10 may be any shape or size needed or desired. For example, as seen in later embodiments, multiple gel-packs 10 are configured for insertion into a vest or other article of clothing worn by a user. In such embodiments, the size and/or shape of gel-pack 10 may be at least partially determined by the size and shape of the pocket that will contain the gel-pack 10 and/or its location in the vest and position over the user's body.

Figure 3:
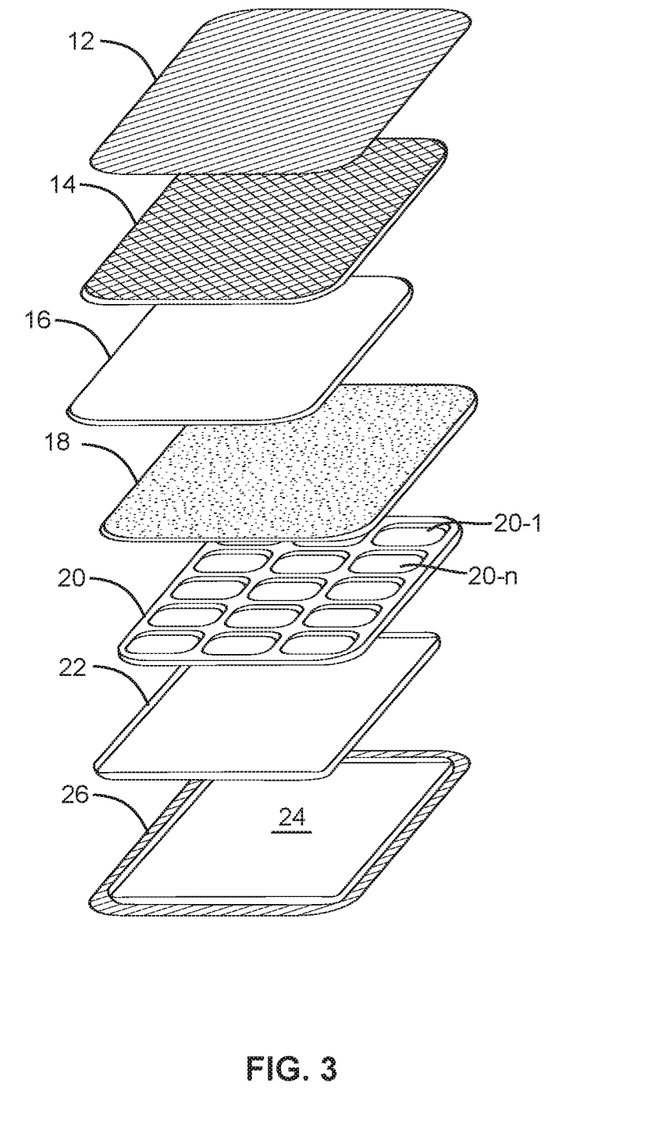
FIG. 3 illustrates the various layers of a gel-pack arranged in a selected order according to one embodiment of the present disclosure.
Figure 4:
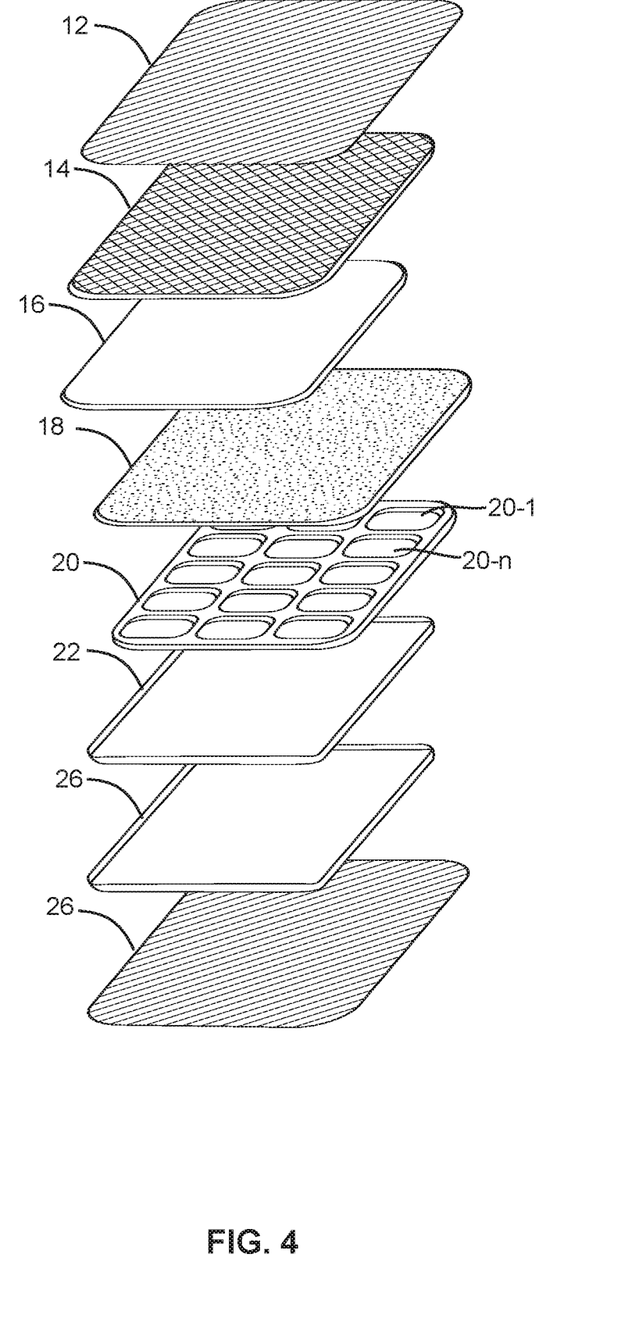
FIG. 4 illustrates the various layers of a gel-pack arranged in a selected order according to another embodiment of the present disclosure.
Figure 5:
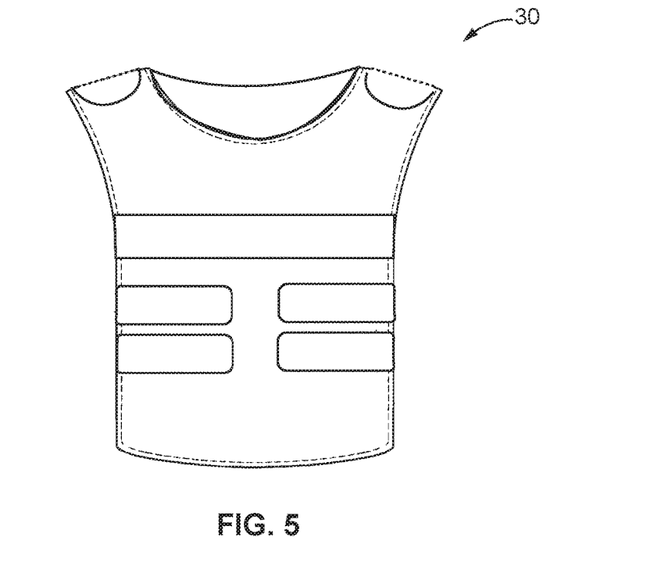
FIG. 5 is a perspective view of an article of clothing suitable for use with embodiments of the present disclosure.
Figure 6A:
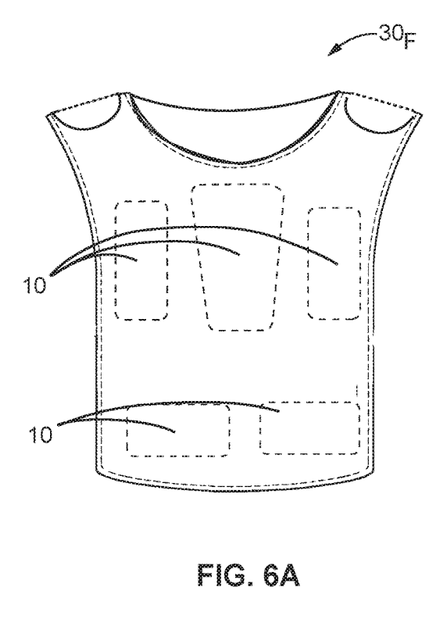
FIG. 6A-6B are perspective views illustrating front and back views, respectively, of an article of clothing equipped with gel-packs according to one embodiment of the present disclosure.
Figure 6B:
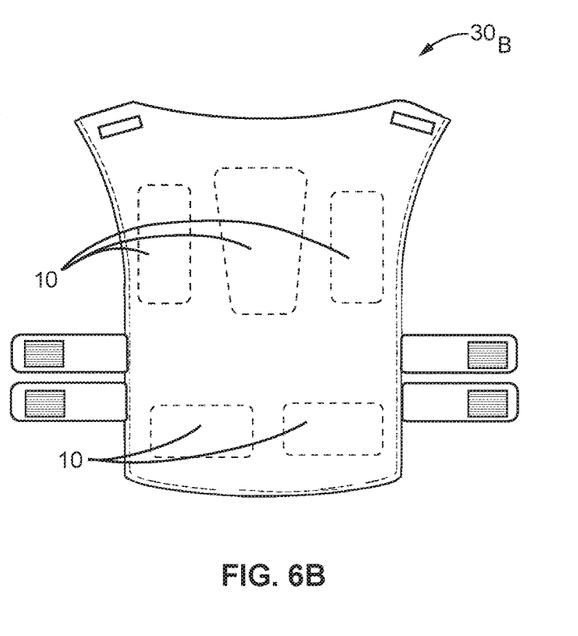
Figure 7:
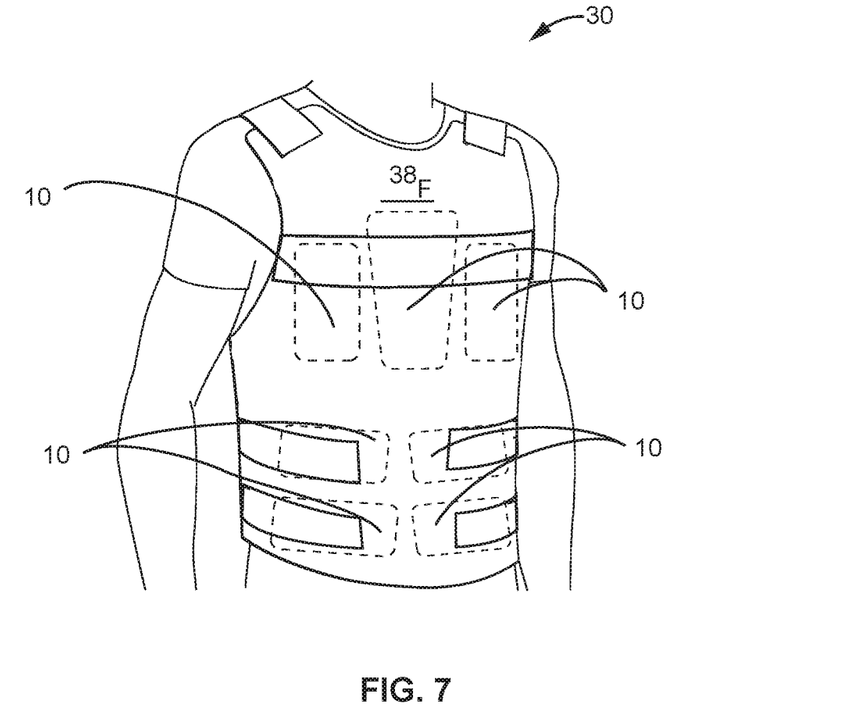
FIG. 7 is a perspective view of a user wearing a body armor vest equipped with gel-packs according to one embodiment of the present disclosure.

FIGS. 3 and 4 illustrate the various self-contained layers of a gel-pack 10 arranged in a particular order according to various embodiments of the present disclosure. Particularly, as seen in the embodiment of FIG. 3, the plurality of self-contained layers comprises the first shell layer 12, an exterior radiant energy deflection barrier layer 14, an insulation layer 16, an interior radiant energy barrier layer 18, a solid gel high thermal capacity (HTC) layer 20, a first semi-solid gel layer 22, and a second semi-solid gel layer 24 that is laminated to a surface of the second shell layer 26. In the embodiment of FIG. 4, the layers are arranged in the same order, but the second semi-solid gel layer 24 comprises a stand-alone component independent of the second shell layer 26. Regardless of the embodiment, however, the ordering and functions of the various layers FIGS. 3-4 are the same.

The first shell layer 12 in this embodiment comprises a waterproof, breathable material configured to allow perspiration and condensation vapor molecules to move outwardly away from the interior of the gel-pack 10, while preventing water and moisture molecules from outside the gel-pack 10 to pass through to the interior of the gel-pack 10. Not only does this help to keep the user dry, but it also prevents molding and material degradation within the interior layers of gel-pack 10. Such a material may comprise, for example, a synthetic polymer such as nylon. In the configuration of FIGS. 3 and 4, the first shell layer 12 forms an "outer" layer of gel-pack 10 that is positioned farthest from the body of the user. That is, the first shell layer 12 comprises a surface of gel-pack 10 that faces away from the user and towards the surrounding environment. In these embodiments, the exterior surface of the first shell layer 12 may be white or some similar color to help reflect ambient radiant energy away from the user's body. This helps gel-pack 10 to maintain the user's body core temperature within a safe, healthy range.

The exterior radiant energy barrier layer 14 is disposed next to the interior surface of the "outer" first shell layer 12 between the other layers of gel-pack 10 and the outer first shell layer 12. The exterior radiant energy barrier layer 14 comprises a highly polished, aluminized reflective layer designed and positioned to reflect ambient radiant energy emanating from the exterior of the gel-pack 10 away from the remaining "interior" layers of gel-pack 10. A broad range of reflective material can be used to manufacture the exterior radiant energy barrier layer 14. Such materials include, but are not limited to, metallized films which are comprised of a polymer film coated with a thin layer of metal.

One example of a suitable metallized film is a polyethylene terephthalate (PET) aluminum foil laminate. In some embodiments, the metallized portion of the film comprises a thin layer of aluminum foil about 0.03 mm thick, while the polymer film comprises a PET film that is about 0.27 mm thick at 380 grams per square meter (GSM). Of course, those of ordinary skill in the art will appreciate that such materials and thicknesses are merely examples, and that other materials and/or thicknesses are also possible.

The insulation layer 16 comprises a closed cell elastomeric thermal insulation foam configured to limit the convection of thermal energy from the exterior environment into the interior layers of gel-pack 10. Any type of insulating material may be used in the manufacture of the insulation layer 16, but in one embodiment, the insulation layer 16 comprises a piece of Neoprene approximately ⅛ of an inch thick, and with a tensile strength of about 1000 pounds/square inch (PSI).

The interior radiant energy barrier layer 18 also comprises a metallized polymer film (e.g., an aluminized film), but is positioned within the gel-pack 10 so as to focus radiant energy emitted from the user's body back into a solid gel HTC layer 20 of gel-pack 10. Particularly, the interior radiant energy barrier layer 18 is positioned within the interior chamber C formed by the first and second shell layers 12, 26 so as to "wrap" the solid gel HTC layer 20 on at least three sides. So disposed, the interior radiant energy barrier layer 18 reflects the thermal energy emitted by the user's body, or by the solid gel HTC layer 20, back into the solid gel HTC layer 20. Thus, as described in more detail below, the solid gel HTC layer 20 functions to "store" energy that is utilized by the gel-pack 10 to regulate the user's core body temperature.

The solid gel HTC layer 20 comprises a solid state gel layer that is fused with a solid state thermal recharge source. In one or more embodiments, this layer comprises a compartmentalized, segmented component layer that stores the gel in each of a plurality of compartments 20-1 . . . 20-n. Such a compartmentalized, segmented structure allows for the flexibility of the gel-pack 10 by allowing for the layer to conform to the user's body as he or she moves.

Additionally, as seen in the figures, the solid gel HTC layer 20 is sandwiched directly between the interior radiant energy barrier layer 18 and a surface of the first semi-solid gel layer 22. This particular arrangement allows the solid gel HTC layer 20 to store thermal energy reflected by the interior radiant energy barrier layer 18. As previously discussed, thermal energy being emitted from the solid gel HTC layer 20 is largely reflected by the interior radiant energy barrier layer 18 back into the solid gel HTC layer 20. This facilitates the capability of the solid gel HTC layer 20 to store thermal energy, as well as to "recharge" one or both of the first and second semi-solid gel layers 22, 24.

The solid gel HTC layer 20 comprises a high density, solid state thermal capacity source configured as a rechargeable thermal energy component that efficiently transfers and stores the thermal and associated radiant energy of a controlled duration. The solid gel HTC layer 20 can be manufactured from of a variety of substances or materials. However, in one embodiment, the solid gel HTC layer 20 comprises a mixture of water, glycerine, methyl paraben, and neutralized carbopol resin.

The first semi-solid gel layer 22 and the second semi-solid gel layer 24 are also flexible layers. This helps the gel-pack 10 to allow for user movement and conform to the user's body. Additionally, both semi-solid gel layers 22, 24 are highly thermally conductive, generally flat, and have a lower thermal capacity than the solid gel HTC layer 20. Further, each of these semi-solid gel layers 22, 24 is comprised of a gel material that is able to store a degree of thermal capacity on its own, and may be manufactured to have variable thicknesses; however, both layers will meet the current average thermoregulatory requirements when they are ¼ inch thick.

As stated previously, one or both of the first and second semi-solid gel layers 22, 24 is configured to be recharged by thermal energy radiated from the solid state gel of solid gel HTC layer 20. That is, one or both of the semi-solid gel layer(s) is configured to store thermal energy emitted by the solid gel HTC layer 20. Additionally, however, one or both of the semi-solid gel layers 22, 24 is also configured to be "recharged" by thermal energy being radiated by the user's body. Thus, the first semi-solid gel layer 22 is positioned within the gel-pack 10 between the user's body and the solid state HTC layer 20, and more particularly, sandwiched directly between the solid gel HTC layer 20 and the second semi-solid gel layer 24.

Additionally, in at least one embodiment, one or both of the semi-solid gel layers 22, 24 function as a "buffer layer" between the higher thermal capacity solid state gel HTC layer 20 and the second shell 26, which will be generally closest to the surface of the user's skin when gel-pack 10 is worn by the user in an article of clothing. Further, in some embodiments, each of the semi-solid gel layers 22, 24 and the solid gel HTC layer 20 are individually contained within sealed bags constructed from Polyvinylchloride (pvc).

The gels used in the construction of the various gel-based layers may be any type of gel needed or desired. In one embodiment, however, the gels utilized in these layers comprise a mixture of 5-Chloro-2-methyl-3(2H)-isothiazolone (CIT) (CAS No. 26172-55-4) with 2-Methyl-3(2H)-isothiazolone (MIT) (CAS No. 2682-20-4) (3:1) (CAS NO. 55965-84-9) Synonym: Kathon 886.

In accordance with the present embodiments, insulation need not be used between the semi solid gel layers 22, 24 and the skin of the user as the conductive cooling effect of the gel-pack 10 layers is advantageous in many applications. Particularly, via the particular arrangement of the gel-based layers, gel-pack 10 is configured to be more readily controllable than other devices aimed at cooling a user. Further, the solid gel HTC layer 20, the first semi-solid gel layer 22, and the second semi-solid gel layer 24 comprise a recessed casing that produces a flat and uniform pad-like layer. This particular structure helps to maximize the surface area of the layer, and therefore, the conductive properties of the layer. In some embodiments, the thickness of the semi solid gel layers, and/or the capacity of the solid gel HTC layer 20, can be manipulated to store a desired thermal capacity, and to achieve a thermoregulatory effect having a desirable duration and intensity.

The second shell layer 26, as previously described, is disposed closest to the user's skin when gel-pack 10 is worn along with the user's clothing, and thus, comprises a surface that faces the user. Thus, in at least one aspect, second shell layer 26 is constructed from a mesh material or wicking fabric, for example, that is configured to allow the user's skin to perspire and breathe. Such materials generally draw moisture away from the user's body, thereby keeping the user dry and helping to prevent molding and degradation of the materials comprising the different sandwiched layers disposed on the interior of gel-pack 10.

FIGS. 5, 6A-6B, and 7 illustrate one embodiment of the present disclosure in which a ballistic vest 30 worn by a user is configured with a plurality of the multi-layer gel-packs 10. As seen in these figures, the gel-packs 10 may be disposed on the interior of one or both of the front 30F and back 30B sides of vest 30. Additionally, any number of gel-packs 10 may be placed anywhere on vest 30, and in any orientation needed or desired. In this embodiment, however, each of a plurality of gel-packs 10 is positioned in the vest 30 so it lies directly over, and covers, an area of the user's core. So disposed, the gel-packs 30 are configured to help regulate the body core temperature of the user such that it is maintained within a healthy, safe range.

Figure 8:
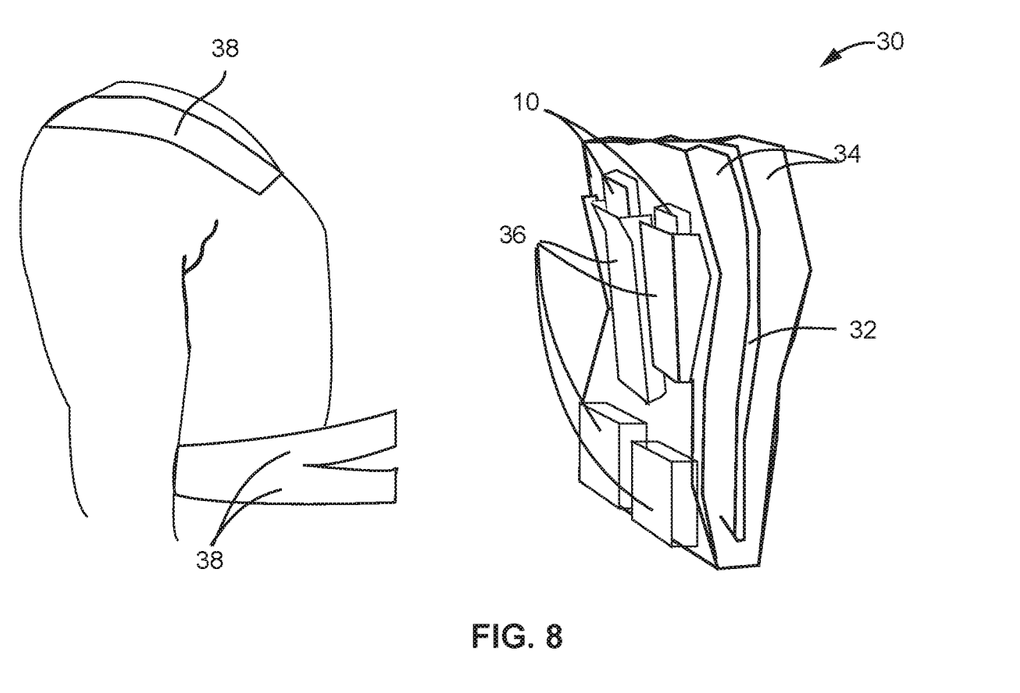
FIG. 8 illustrates a body armor vest equipped with gel-packs according to one embodiment of the present disclosure.

FIG. 8 illustrates a side view of vest 30 configured with a plurality of gel-packs 10 in accordance with embodiments of the present disclosure. As seen in FIG. 8, vest 30 is specifically configured as an anti-ballistic article of clothing, and thus, comprises a ballistic panel 32 sandwiched between layers of KEVLAR covered foam 34, for example. Any material needed or desired may be utilized for the ballistic panel 32 in vest 30. Such materials include, but are not limited to, multiple layers of KEVLAR, one or more ceramic panels, and the like.

Vest 30 may have a tendency to increase the body core temperature of a user when worn for long periods of time. Such body temperature increases could further be exacerbated by the user's physical exertion while wearing vest 30. However, according to the present disclosure, the user may insert a plurality of gel-packs 10 into corresponding pockets formed in an interior surface of the vest 30. So inserted, the gel-packs 30 help regulate the user's core body temperature, as previously described.

Particularly, the exterior radiant energy barrier layer 14 reflects thermal energy from the exterior environment away from the interior of the gel-pack 10, while the insulation layer 16 limits the convection of residual thermal energy that may have passed through the exterior radiant energy barrier layer 14 into the interior layers of gel-pack 10. The interior radiant energy barrier layer 18 reflects thermal energy emitted by the user's body into the solid gel HTC layer 20, where it is stored. The first and second semi-solid gel layers 22, 24 conduct the thermal energy being emitted by the user away from the user's body so that it is stored in the solid gel HTC layer 20. By storing thermal energy in the solid gel HTC layer 20, each gel-pack 10 helps keep the user cool and regulate his or her body temperature by preventing the user from overheating.

As stated previously, one or more of the layers in gel-pack 10 are "rechargeable." That is, the layers of gel-pack 10 are self-contained, individual components. According to the present disclosure, a user may remove one or more of the layers, individually, and place them into a freezer or refrigerator or any device capable of cooling the materials that comprise these layers. For example, in one embodiment, a user may remove one or more of the first semi-solid gel layer 22, the second semi-solid gel layer 24, and the solid gel HTC layer 20 from the interior pocket of a gel-pack 10 simply by pulling these layers out of the pocket formed by the first and second shell layers 12, 26. The user may then "recharge" these layers by placing them into a freezer, for example, and replace them in gel-pack 10 with other layers that have already been "recharged."

In other embodiments, the gel-pack 10 of the present disclosure can help keep a user warm. In these embodiments, the interior radiant energy barrier layer 18 reflects the thermal energy emitted by the user's body back into the HTC layer 20, where it is stored as previously described. However, the HTC layer 20 will also radiate thermal energy, which is received and stored by the first and second semi-solid gel layers 22, 24. Thus, the first and second semi-solid gel layers 22, 24 are "recharged" from the thermal energy radiated by the HTC layer 20. In these embodiments, the HTC layer 20 may be heated externally and then inserted into the interior chamber C of gel-pack 10.

Alternatively, in embodiments where the gel-packs 10 are closed so that the individual component layers cannot be removed from inside gel-pack 10, the entire gel-pack 10 is rechargeable by placing the gel-pack into a freezer. In these embodiments, users are still able to replace gel-packs 10 simply by removing one gel-pack 10 from its pocket in vest 30 and replacing it with another, recharged gel-pack 10.

In addition to the benefits gel-pack 10 provides with respect to regulating a user's core body temperature, gel-pack 10 also enhances the benefits provided by vest 30 by assisting vest 30 in absorbing impact energy. More specifically, in the event that a projectile (e.g., a bullet) hits the vest 30 worn by the user, the presence of the gel-packs 10 adds an additional layer of protection. Particularly, the gels that comprise the various layers of gel-pack 10 help to absorb any residual energy of a projectile impacting vest 30, as well as dissipate that energy across the area of the gel-pack 10. So absorbed and/or dissipated, the force felt by a user as a result of a projectile striking vest 30 configured with one or more gel-packs 10 of the present disclosure is greatly reduced, thereby diminishing the extent of the bruising and other such injuries experienced by the user.

The present invention may, of course, be carried out in other ways than those specifically set forth herein without departing from essential characteristics of the invention. Therefore, the present embodiments are to be considered in all respects as illustrative and not restrictive, and all changes coming within the meaning and equivalency range of the appended claims are intended to be embraced therein.

What is claimed is:

1. A multi-layer gel-pack for regulating a core body temperature of a user, the gel-pack comprising:
   a casing having a first surface configured to face towards a user and an opposing second surface configured to face away from the user; and
   a plurality of components disposed as layers within the casing and comprising:

a thermal energy storage component configured to store thermal energy radiating from a user's body;

a first radiant energy barrier disposed between the thermal energy storage component and the second surface of the casing, and configured to prevent the transfer of thermal energy radiating from an exterior of the casing into the thermal energy storage component; and a second radiant energy barrier disposed between the thermal energy storage component and the first radiant energy barrier, and configured to reflect the thermal energy radiating from the user's body into the thermal energy storage component;

a first semi-solid gel component disposed between the first surface of the casing and the thermal energy storage component; and a second semi-solid gel component disposed between the first semi-solid gel component and the thermal energy storage component; and wherein each component is a stand-alone component configured to be inserted into the casing, and removed from the casing, independently of the other components.

2. The multi-layer gel-pack of claim 1 wherein the plurality of components further comprises a thermal insulation component disposed between the first and second radiant energy barriers, and wherein the thermal insulation component is configured to prevent the transfer of thermal energy that radiates through the first radiant energy barrier into the thermal energy storage component.

3. The multi-layer gel-pack of claim 1 wherein the first and second semi-solid gel components are configured to transfer the thermal energy radiating from the user's body into the thermal energy storage component.

4. The multi-layer gel-pack of claim 1 wherein one or both of the first and second semi-solid gel components are configured to store thermal energy radiated by the thermal energy storage layer.

5. The multi-layer gel-pack of claim 1 wherein the first semi-solid gel component is attached to an interior surface of the casing.

6. The multi-layer gel-pack of claim 1 wherein one or both of the first and second semi-solid gel components comprise a peripheral wall forming a recess configured to contain the semi-solid gel.

7. The multi-layer gel-pack of claim 1 wherein the first and second surfaces of the casing comprise, respectively, first and second shell layers affixed to each other at peripheral edges to form a pouch into which the plurality of components are removably disposed.

8. The multi-layer gel-pack of claim 7 wherein:
the first shell layer is configured to be positioned nearest the user's body and to allow vapor molecules to move outwardly away from the user's body; and
the second shell layer is configured to be positioned farthest from the user's body and to allow the vapor molecules to move outwardly away from an interior of the casing, and to prevent moisture from entering the casing.

9. The multi-layer gel-pack of claim 7 wherein the casing further comprises an opening formed by the first and second shell layers, and wherein the opening is configured such that selected components are inserted into the pouch, and removed from the pouch, through the opening.

10. The multi-layer gel-pack of claim 1 wherein the thermal energy storage component comprises a gel configured to store the thermal energy emitted by a user's body.

11. The multi-layer gel-pack of claim 10 wherein the thermal energy storage component comprises a plurality of individual compartments, with each compartment configured to hold a portion of the gel.

12. The multi-layer gel-pack of claim 1 wherein the second radiant energy barrier comprises a peripheral wall forming a recess sized to receive the thermal energy storage component, and is configured to focus the thermal energy radiated by the user's body into the thermal energy storage component.

13. A multi-layer gel-pack for regulating a core body temperature of a user, the gel-pack comprising:
a casing comprising an interior chamber formed between first and second exterior surfaces, wherein the first exterior surface is configured to face towards the user and wherein the second exterior surface is configured to face away from the user;
a high thermal capacity (HTC) layer disposed within the interior chamber, wherein the HTC layer comprises one or more individual compartments with each compartment comprising a gel configured to store thermal energy radiated by the user's body;
a first metallized reflective layer disposed within the interior chamber between the HTC layer and the casing, wherein the first metallized reflective layer reflects ambient thermal energy away from the HTC layer;
a second metallized reflective layer disposed within the interior chamber between the HTC layer and the first metallized reflective layer, and configured to focus the thermal energy radiated by the user's body into the one or more individual compartments of the HTC layer; and
first and second semi-solid gel layers disposed between the first exterior surface and the HTC layer.

14. The multi-layer gel-pack of claim 13 wherein one or more of the HTC layer, the first metallized reflective layer, and the second metallized reflective layer is a stand-alone component.

15. The multi-layer gel-pack of claim 14 wherein the one or more of the HTC layer, the first metallized reflective layer, and the second metallized reflective layer is configured to be inserted into, and removed from, the interior chamber by the user.

16. The multi-layer gel-pack of claim 13 wherein the second metallized reflective layer is configured to receive at least a portion of the HTC layer, and comprises a shape that focuses the thermal energy radiated by the user's body into the HTC layer.

17. A method of assembling a multi-layer gel-pack for regulating a core body temperature of a user, the method comprising:
inserting a thermal energy storage component into an interior of a casing, wherein the thermal energy storage component is configured to store thermal energy that radiates from the user;
inserting a first radiant energy barrier into the interior of the casing between the thermal energy storage component and the casing, wherein the first radiant energy barrier prevents the transfer of ambient thermal energy into the thermal energy storage component; and
inserting a second radiant energy barrier into the interior of the casing between the thermal energy storage component and the first radiant energy barrier, wherein the second radiant energy barrier reflects the thermal energy radiating from the user's into the thermal energy storage component;

inserting first and second semi-solid gel layers between an exterior surface of the casing and the thermal energy storage component; and wherein each of the thermal energy storage component and the first and second radiant energy barriers are stand-alone components configured to be inserted into the interior of the casing independently of each other.

* * * * *